April 15, 1975 T. YUGE Plant Pat. 3,704
AZALEA PLANT
Filed April 10, 1974
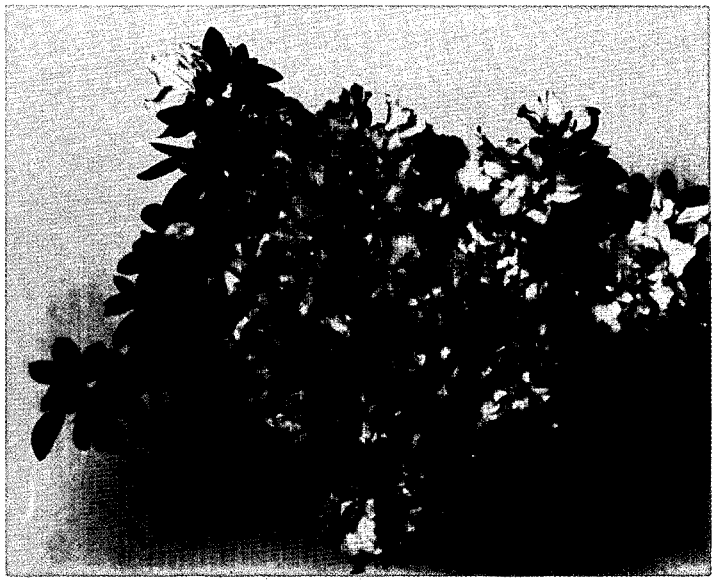
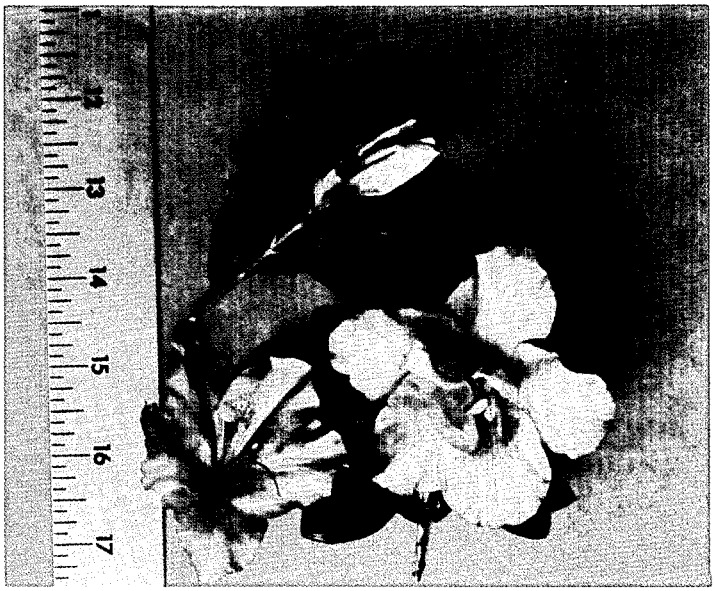

United States Patent

Plant Pat. 3,704
Patented Apr. 15, 1975

3,704
AZALEA PLANT

Takeo Yuge, Altadena, Calif., assignor to Geo. J. Ball, Inc., Chicago, Ill.

Filed Apr. 10, 1974, Ser. No. 459,656
Int. Cl. A01h *5/00*
U.S. Cl. Plt.—56 1 Claim

ABSTRACT OF THE DISCLOSURE

A new variety of azalea plant distinguished by its profuse production of exceptionally bright pink blossoms and its compact and branching growth habit which makes it particularly suitable for greenhouse pot forcing for the commercial trade.

BACKGROUND OF THE INVENTION

My new variety of azalea plant originated as a seedling resulting from a cross of one of my own seedlings named Kaho (unpatented) and another unpatented variety named Dr. Bergman, this breeding being done at Altadena, Calif., in the course of extensive breeding efforts being carried on by me with the object of producing improved types of greenhouse pot-forcing azaleas capable of profuse production of attractive blossoms for the commercial trade. This plant was selected for propagation and test because of its attractive growth habit, its full form and its profuse production of bright pink flowers and extensive asexual propagation of the new plant, at Altadena, Calif., by me and under my direction, through many generations by means of vegetative cuttings from successive plants has demonstrated that its distinguishing characteristics of growth habit and flower coloration hold true from generation to generation and therefore appear to be permanently fixed. Commercial propagation of this new plant, by means of cuttings, is now being done at Salem and Woodburn, Oreg., and at San Fernando, Calif.

DESCRIPTION OF THE DRAWING

This new variety of azalea plant is illustrated by the accompanying full color photographic drawing in which the upper view shows a potted plant in full bloom and the lower view shows, in more detail, a bud and a pair of fully opened blossoms. The colors shown are as nearly true as can be obtained through the use of conventional photographic procedures.

DESCRIPTION OF THE NEW PLANT

The following is a detailed description of my new variety of azalea plant with color designations according to Robert F. Wilson's Horticultural Colour Chart issued by the British Colour Council in collaboration with The Royal Horticultural Society at London, England.

The plant

Origin: Seedling
Parentage:
*Seed parent.*—Kaho (an unpatented seedling discovered by me).
*Pollen parent.*—Dr. Bergman (unpatented).
Classification:
*Botanic.*—Rhododendron.
*Commercial.*—Hybrid azalea for greenhouse pot forcing.
Form: Bush—as a potted plant.
Height: Medium.
Growth: Sturdy, upright, vigorous and compact.
Branching: Profusely branched.
Foliage: Quantity—abundant.
*Leaf shape.*—Acute apiculate apex with acuminate or attenuate base. In general—elliptic.

*Leaf size.*—1¾ to 2 inches long.
*Texture.*—Leathery and puberous.
*Aspect.*—Glossy.
*Ribs and veins.*—Alternate. Veins are more visible on under side.

| | Young leaf | Mature leaf |
|---|---|---|
| Color: | | |
| Upper side | Spinach Green 0960/1 | Ivy Green 0001060/3. |
| Under side | Spinach Green 0960/3 | Spinach Green 0960/3. |

*Petioles.*—¼ to ⅜ inch long. Flat topped and hirsute. Hairs are silvery on new leaves and brown on mature leaves.

The bud

Form: Elliptical, long and pointed.
Size: Medium. About 1¼ inch long and about ½ inch in diameter.
Opening rate: The bud opens slowly.
Color:
*When sepals first divide.*—Spirea Red 025/1.
*When petals begin to unfurl.*—Solferino Purple 26/1.
Sepals: Upstanding and lanceolate. Hairy on outside.
*Color.*—Inside and outside: Scheeles Green 860/3.
Calyx: Star shaped with 5 lobes. Small in size and having a very tomentose aspect.
Peduncle: Erect and slender. About ¼ to 5/16 inch long, Pod Green 061/1 in color and very tomentose.

The flower

Blooming habit: Recurrent. Blooming once, from mid-season to late Spring with profuse production of blossoms.
Size: Medium. Up to 2½ inches in diameter and 1½ to 1¾ inches in depth.
Borne: In clusters.
Shape: Funnel shaped when bloom first opens, changing to a broader funnel form as blossom matures.
Petalage: Number—5 or 6 large fused and connate outer petals in overlapping arrangement.
*Form.*—Semi-double funnel form, slightly undulate at outer edges.
*Color.*—Body—Solferino Purple 26/2 with edges of Solferino Purple 26. Standard and upper wings are flecked or streaked with Tyrian Purple 727. Reverse side—China Rose 024/1 shading into China Rose 024.
*Texture.*—Soft. Appearance: Satiny.
Petaloids: 2 to 8 in number, but may be connate.
*Size.*—⅜ to 1 inch long.
*Color.*—China Rose 024/1. Some flecked with Tyrian Purple 727.
Peduncle: Sturdy, upright and tomentose. ¼ to 5/16 inch long.
*Color.*—Pod Green 061/1, slightly tinged with Spirea Red 025/2.
Persistence: Petals hang on and dry.
Fragrance: None.
Disease resistance: Resists all known diseases prevalent in all areas where this plant is being grown.
Lasting quality: Very goor on plant.

Reproductive organs

Stamens:
*Filaments.*—From none to 2 in number, any others being fused to petaloids. Length—⅝ inch. Color—Rose Opal 022/3.
*Anthers.*—One 2-celled sac, 1/16 inch long, on each filament.
*Pollen.*—Occasional minuscule amount—White in color.

Pistils: One—1 to 1 7/16 inch long.

*Style.*—Color—Rose Opal 022/1.

*Stigma.*—Color—Varies from Indian Lake 826 to Citron Green 763/2.

Ovaries: Superior and tomentose.

Fruit: None observed.

I claim:

1. A new and distinct variety of azalea plant substantially as herein shown and described, characterized by its vigorous, profusely branched and compact growth habit as a greenhouse pot-forcing azalea, and by its profuse production of bright pink blossoms.

No references cited.

ROBERT E. BAGWILL, Primary Examiner